United States Patent
Knott et al.

(10) Patent No.: US 9,782,503 B2
(45) Date of Patent: Oct. 10, 2017

(54) APPARATUS AND METHOD FOR THE STERILIZATION OF CONTAINERS

(71) Applicant: KRONES AG, Neutraubling (DE)

(72) Inventors: Josef Knott, Schierling (DE); Hans Scheuren, Bad Kreuznach (DE); Jochen Krueger, Hagelstadt (DE)

(73) Assignee: KRONES AG (DE)

( * ) Notice: Subject to any disclaimer, the term of this patent is extended or adjusted under 35 U.S.C. 154(b) by 89 days.

(21) Appl. No.: 14/632,097

(22) Filed: Feb. 26, 2015

(65) Prior Publication Data

US 2015/0238643 A1 Aug. 27, 2015

(30) Foreign Application Priority Data

Feb. 26, 2014 (DE) .................... 10 2014 102 537

(51) Int. Cl.
| | |
|---|---|
| *A61L 2/08* | (2006.01) |
| *B65B 55/08* | (2006.01) |
| *G21K 5/10* | (2006.01) |
| *G21K 5/08* | (2006.01) |
| *B65B 43/50* | (2006.01) |

(52) U.S. Cl.
CPC .............. *A61L 2/087* (2013.01); *B65B 55/08* (2013.01); *G21K 5/10* (2013.01); *A61L 2202/23* (2013.01); *B65B 43/50* (2013.01); *G21K 5/08* (2013.01)

(58) Field of Classification Search
CPC ...................................................... A61L 2/087
USPC ......................................................... 422/22
See application file for complete search history.

(56) References Cited

U.S. PATENT DOCUMENTS

| | | | |
|---|---|---|---|
| 8,453,419 B2 | 6/2013 | Roithmeier et al. | 53/426 |
| 8,708,680 B2 | 4/2014 | Geltinger et al. | 425/3 |
| 8,728,393 B2 | 5/2014 | Knott et al. | 422/22 |
| 8,729,499 B2 | 5/2014 | Knott et al. | 250/455.11 |
| 2009/0134338 A1 | 5/2009 | Eguchi et al. | 250/396 R |
| 2010/0034985 A1 | 2/2010 | Krueger et al. | 427/579 |
| 2010/0071724 A1 | 3/2010 | Baumgartner et al. | 134/23 |

(Continued)

FOREIGN PATENT DOCUMENTS

| | | | |
|---|---|---|---|
| CN | 103253411 | 8/2013 | B65C 3/14 |
| DE | 102008054110 | 5/2010 | A61L 2/08 |

(Continued)

OTHER PUBLICATIONS

Chinese First Office Action issued in application No. 201510087465.X, dated Dec. 23, 2016 (14 pgs).

*Primary Examiner* — Kevin Joyner
*Assistant Examiner* — Holly Mull
(74) *Attorney, Agent, or Firm* — Hayes Soloway P.C.

(57) ABSTRACT

A sterilization device has a rod-like body which is capable of being introduced through an aperture into an interior space of containers and which acts upon an inner wall of the containers with radiation. A lifting cam produces a movement in a longitudinal direction, of the containers between the containers and the sterilization device in such a way that the containers are capable of being guided over the rod-like body. A movement device is provided which is capable of producing a relative movement in the longitudinal direction of the containers between the rod-like body and the lifting cam and of altering a relative distance between the lifting cam and the rod-like body.

19 Claims, 1 Drawing Sheet

(56) References Cited

U.S. PATENT DOCUMENTS

| | | | | |
|---|---|---|---|---|
| 2012/0219455 | A1* | 8/2012 | Meinzinger | A61L 2/087 |
| | | | | 422/22 |
| 2013/0216430 | A1* | 8/2013 | Knott | A61L 2/087 |
| | | | | 422/22 |
| 2015/0023838 | A1* | 1/2015 | Keikhaee | B65B 55/10 |
| | | | | 422/24 |
| 2016/0083131 | A1* | 3/2016 | Yokobayashi | A61L 2/087 |
| | | | | 250/454.11 |

FOREIGN PATENT DOCUMENTS

| | | | | |
|---|---|---|---|---|
| DE | 102009041215 | 3/2011 | | A61L 2/18 |
| DE | 102010022130 | 11/2011 | | B29C 49/42 |
| DE | 102011055553 | 5/2013 | | A61L 2/08 |
| DE | 102011056162 | 6/2013 | | A61L 2/08 |
| EP | 1 403 186 | 3/2004 | | B65B 39/00 |
| EP | 1 956 608 | 8/2008 | | G21K 5/04 |
| EP | 2 151 510 | 2/2010 | | A61L 2/14 |
| WO | WO 2008/034512 | 3/2008 | | A61L 2/00 |

\* cited by examiner

APPARATUS AND METHOD FOR THE STERILIZATION OF CONTAINERS

BACKGROUND OF THE INVENTION

The present invention relates to an apparatus and a method for the sterilization of containers. Apparatus and methods of this type have long been known from the prior art. Attempts have been made in recent years to dispense with the possibility of using chemical sterilization agents or at least to reduce this use. In recent years sterilization devices have also been known which act upon the walls of the containers to be sterilized with a radiation, and in particular a charge carrier radiation. The present invention is described essentially with reference to radiators of electrons, but it should be pointed out that an application of the invention is also optionally possible in the case of other charge carriers, such as for example protons or alpha particles. In addition, other types of radiation, such as x-rays or UV radiation, could also be used.

Apparatus and methods are known from the prior art in which radiation fingers are inserted—by way of the apertures of the containers to be sterilized—into the aforesaid containers. These radiation fingers usually have in this case an outlet window for charge carriers, such as in particular electrons. It is advantageous in this case for the outlet window to be arranged on an underside of the respective radiation fingers. On the one hand these radiation fingers must have in this case a cross-section which is capable of being inserted into the container through the aperture. On the other hand these radiation fingers must usually also maintain in the interior thereof a vacuum inside which the charge carriers can be accelerated. This leads to radiation fingers of this type frequently being very delicate and also expensive appliances. On account of the low mechanical loading capacity the costs in the event of one-off light or even severe damage are also very high.

Furthermore, sterilization devices which use radiation, and in particular electron beams, for sterilization purposes usually have an electron production device, and also an acceleration device which accelerates the charge carriers (in particular inside a/the vacuum) in the direction of the outlet window.

In the same way, apparatus are known from the prior art in which the sterilization devices are arranged on a movable carousel. In addition, the containers and, in particular, preforms are arranged on a movable carousel by way of clamps. For the internal sterilization each individual container is moved on the clamps by way of the sterilization device or the radiation finger associated with the sterilization devices respectively. In this case an electric motor, which handles a drive profile individually during the treatment cycle, is available in each case (for example on the carousel) in order to produce the movement of the respective clamp.

A drawback in the case of the prior art, however, is that linear motors are very expensive and the outlay of the control and programming (for example in order to produce the drive profile) is enormous, but no mechanical parts have to be changed in the event of a change in format of the containers.

The object of the present invention is therefore to overcome these drawbacks and to provide an apparatus as well as a method, which at the same time is capable of being used or modified respectively in an inexpensive and nevertheless flexible manner and can be used for the sterilization of widely differing formats of containers.

In this case, however, the aperture of the container should remain substantially the same or should at least have a certain minimum cross-section, since the rod-like body or radiation finger respectively must be capable of still being guided securely in the container, so that containers of different lengths and diameters can be sterilized in an inexpensive manner by the apparatus.

SUMMARY OF THE INVENTION

An apparatus according to the invention for the sterilization of containers has a sterilization device which has a rod-like body which is capable of being introduced through an aperture of the containers into an interior space of the containers and which acts upon an inner wall of the containers with radiation, in particular with charge carriers and in particular with electrons. The rod-like body in this case is, in particular, a radiation finger. Furthermore, the apparatus has a lifting cam which produces a movement in a longitudinal direction L of the containers between the containers and the sterilization device in such a way that the containers are capable of being guided by way of the rod-like body. It is thus preferable for an apparatus for the internal sterilization of containers to be involved.

In this way, it is preferable for the lifting cam to produce a movement, and in a particularly preferred manner only a lifting movement in the longitudinal direction L, of the containers, by which the containers are guided/moved or are capable of being guided/moved respectively over the rod-like body or radiation finger respectively. The introduction of the radiation finger into the containers is therefore carried out by a movement and preferably only by a movement of the containers, this movement (the lifting movement in the longitudinal direction L) preferably being carried out and/or provided only by the lifting cam. It is particularly preferred for the lifting cam to be a fixed lifting cam, the course of which in a particularly preferred manner cannot be altered. In this case the clamps run over these lifting cams, as a result of which a fixed driving or movement profile is achieved.

A "transfer" or a "transmovement" is preferably understood in this case as being that the rod-like body is introduced/inserted at least locally into the container or the interior space/the interior respectively of the container, this introduction/insertion being preferably produced by a movement of the container and not by a movement of the sterilization device and/or of the rod-like body. Furthermore, it can preferably be understood as a guidance or movement respectively of the container over the rod-like body from below the rod-like body (or the container opening is directed upwards, away from the centre of the Earth respectively), in which case however a movement from above and over the rod-like body would also be possible (or the container opening is directed downwards, towards the centre of the Earth respectively). Other arrangements or orientations respectively, however, which would extend obliquely in this way, would also be possible. In this case, however, the corresponding elements extend further in the longitudinal direction L, but essentially only this longitudinal direction L is changed, or the direction of movement extends along this longitudinal direction L.

According to the invention the apparatus has a movement device, or a movement device is provided respectively, which is designed and arranged in such a way that a relative movement, in the longitudinal direction L of the containers, between the rod-like body and the lifting cam is capable of being produced and a relative distance r between the lifting cam and the rod-like body is capable of being altered.

It is therefore proposed that the driving profile or movement profile respectively of the containers should be implemented or caused by the lifting cam, which, although less flexible, should nevertheless be substantially less expensive and adequate for most purposes of use of the apparatus. On account of the relative capacity of movement, caused by the movement device, it is, in addition, further possible to ensure in a simple manner that even containers or pre-forms respectively of different length can be sterilized by the apparatus without major modifications/alterations having to be carried out.

Concerning the lifting cams, the problem arises that a fixed driving profile is pre-set, so that in particular relatively short containers cannot be handled, since they (in particular the base thereof) would collide with the radiation finger. This problem is solved by altering the relative distance r between the lifting cam and the rod-like body/radiation finger.

It is preferable for the containers to be plastics material containers such as for example plastic bottles or plastics material pre-forms. It is particularly preferred for the containers to be plastics material pre-forms.

In the case of a preferred embodiment the movement device is designed and arranged in such a way that a pre-determined distance a between a base area of the containers and the rod-like body or the sterilization device respectively is capable of being set. In this way, it is preferable for the movement device to be designed and arranged in such a way that a relative movement in the longitudinal direction L of the containers between the rod-like body or the sterilization device respectively and the lifting cam is capable of being produced and a relative distance r between the lifting cam and the rod-like body or the sterilization device respectively is capable of being altered, in such a way that a pre-determined distance a between a base area of the containers and the rod-like body is capable of being set.

It is preferable for the distance between the base area of the containers and the rod-like body to be capable of being set outside a working operation.

Accordingly, it is preferable for the relative movement in the longitudinal direction L between the rod-like body or the sterilization device respectively and the lifting cam to be used in order to be able to set a pre-determined distance a between the base area of the container and the rod-like body even in the case of containers of different length.

In this case the distance a is preferably detected, determined, measured, established and/or pre-set between a midpoint of the base area, which is preferably situated substantially in the region of the injection point, and the rod-like body (in particular a/the outlet window of the rod-like body). This point, at which the distance a in the longitudinal direction L (of the container) from the base area of the container and the outlet window is established or set respectively, is therefore preferably present at the point at which an axis of symmetry S (this extends in the longitudinal direction L of the container) of the container intersects with the base area. In this case essentially the innermost point of the base is used. In general, however, it would also be possible to use another point of the base area in order to fix the distance a or by which the distance a has been or is described respectively.

As a result of using a lifting cam the containers, and in particular the apertures thereof, are always moved by a pre-determined stroke/path in the longitudinal direction L and over the radiation fingers. If the production is changed over and use is made of other containers which are shorter (the extension thereof in the longitudinal direction L is less), with a pre-determined stroke/path the base area of the containers would move closer to the radiation finger or the end thereof respectively or would even touch the latter, and this would result in considerable damage and cost. The relative distance r between the radiation finger or the end thereof respectively and the lifting cam can now be additionally adjusted by the movement device, so that when shorter containers are used the relative distance r can be increased, as a result of which the pre-determined distance a between the radiation finger or the end thereof respectively and the base area can in turn be set or is capable of being set.

It is preferable for the pre-determined distance a to be present when the containers run over the highest point of the lifting cam or are present on the latter respectively. The highest point can also be a relatively long area (thus a highest area). In this case the highest point is essentially understood as being the point/area at which the lifting cam or areas/parts of the lifting cam respectively is or are at the smallest distance from the radiation finger and/or the sterilization device. Accordingly, the highest point is present at the reversal point in which the containers are transferred from a guide over the rod-like body/radiation finger into a reversed movement in which the containers are pulled off from the radiation finger. It is preferable for the radiation finger and the containers never to touch one another, so that "pulling off" is to be understood as removing the radiation finger from the container. This reversal point can also be present over a specific area or the lifting cam can extend substantially horizontally in this area respectively. By way of example, the container is guided over the radiation finger for sterilization purposes until the pre-determined distance a is reached, then this distance is held for a certain amount of time for sterilization purposes, and then the container is pulled off from the radiation finger again. This is carried out by a raised portion, which is present over a specified area (or extends over a specified length which is dependent upon the speed of conveying the containers), on the lifting cam.

In the case of a further preferred embodiment the sterilization device and/or the rod-like body is movable by the movement device in the longitudinal direction L of the containers and the lifting cam is arranged so as to be immovable. In this way, it turns out to be preferred for the relative movement produced in the longitudinal direction L between the rod-like body and the lifting cam to be produced by a movement of the sterilization device and/or the rod-like body. The movement device is therefore preferably designed and arranged in such a way that the (relative) movement in the longitudinal direction L of the containers between the rod-like body and the lifting cam is capable of being produced by a movement of the sterilization device and/or the rod-like body and, in this way, the relative distance r between the lifting cam and the rod-like body is capable of being altered.

In the case of a preferred embodiment the apparatus has a plurality of sterilization devices with radiation fingers or rod-like bodies respectively which are arranged on a common carrier rotatable about an axis of rotation E, so that the individual radiation fingers/sterilization devices move along a circular (conveying) path. The apparatus is thus preferably a carousel apparatus or the common carrier is designed in the form of a carousel respectively. In addition, it is preferable for the common carrier to be movable by the movement device in the longitudinal direction L. In this way, all/the plurality of sterilization devices are moved with respect to the lifting cam by essentially a single movement device, so that it is possible to dispense with movement devices for each individual sterilization device. In this way, this prevents a plurality of motors having to be used for the various radiation fingers/sterilization devices arranged on a carousel, since the radiation fingers/sterilization devices are capable of being moved by the movement of the carousel as a whole or of the common carrier respectively in accordance with the proposed apparatus (or the proposed method respectively).

It is therefore preferable for the relative movement produced in the longitudinal direction L between the rod-like body or the radiation finger respectively and the lifting cam to be capable of being produced by a movement of the carrier of the plurality of radiation fingers/sterilization devices. The movement device is accordingly preferably designed and arranged in such a way that the (relative) movement in the longitudinal direction L of the containers between the rod-like body and the lifting cam is capable of being produced by a movement of the carrier of the plurality of radiation fingers/rod-like bodies/sterilization devices and the relative distance r between the lifting cam and the rod-like body is capable of being altered.

In this way, the plurality of radiation fingers/sterilization devices are preferably connected to one another mechanically by the common carrier and the radiation fingers/sterilization devices are therefore movable in the same way, and in particular are rotatable about the axis of rotation E and in the longitudinal direction L.

In this way, it is preferable for a base plate (or the common carrier respectively) of the common carousel/the apparatus, on which the sterilization devices are fastened, to be capable of being altered in the height thereof. It is thus possible for example for a container/pre-form which is 20 mm shorter and in which the base plate is raised by 20 mm (in this way the relative distance r is increased) to be treated. As a result, an end position of the radiation finger (the reversal point) is again set to be equal to a container/pre-form base, so the pre-determined distance a remains the same.

Since the residence time of the radiation finger in the container turns out to be shorter in the case of shorter pre-forms, as a result of which the sterilization could possibly not be made sufficient, it is preferably proposed that a speed, at which the container/the pre-form is moved on a flank of the lifting cam and thus in which the radiation finger is present at the end point in the container/the pre-form, should be extended. A further possibility of improving the sterilization would be capable of being achieved by an increase in the dose rate applied, preferably in the same way while the container/the pre-form is moved on a flank of the lifting cam.

In the case of a further preferred embodiment the pre-determined distance is not capable of being altered during the operation of the apparatus. Accordingly, the same type of containers is always sterilized during the operation, so that no alteration is necessary. If, however, a shift is made to the processing of other containers/(plastics material) pre-forms, in particular of containers/(plastics material) pre-forms of different length, the relative distance r between the lifting cam and the radiation finger is altered, so that the pre-determined distance a between the base area of the container to be newly processed and the radiation finger can be adjusted again. It is preferable for the pre-determined distance a to be identical for each container or each (plastics material) pre-form respectively.

In the case of a further preferred embodiment the rod-like body or the radiation finger respectively has an outlet window for charge carriers produced by the sterilization device, by which outlet window the charge carriers escape from the rod-like body, and in this way the inner wall of the containers is acted upon with the charge carriers. This outlet window is situated, as it is generally known from the prior art, on the underside of the radiation finger, therefore on the side which is closest to the lifting cam. In addition, the pre-determined distance a between a base area of the containers and the outlet window of the rod-like body is capable of being set. A distance between the radiation finger/the rod-like body and a further element of the apparatus (for example the lifting cam, the base area) is for the most part described above. This is thus preferably to be understood as being the distance between the outlet window of the radiation finger/the rod-like body and the respective further element. This distance is preferably provided or present respectively (essentially) in the longitudinal direction.

In the case of a further preferred embodiment the containers are fastened to a common element by way of a respective holding device, in particular a holding clamp, which grips the container under or above a carrying ring. The common element is rotatable about an axis of rotation E and the respective holding device is preferably movable in the longitudinal direction (L). In this way, the holding device is movable with respect to the common element in the longitudinal direction L and is arranged on/secured to the latter in a corresponding manner. It is preferable for the common element to be accordingly a carousel element, a rotatable common carrier or a rotatable conveying device which conveys/moves the containers during the sterilization.

The common element preferably has a plurality of holding devices, it being particularly preferred for a number of the plurality of holding devices to correspond to the number of the plurality of sterilization devices, so that one sterilization device is present/arranged on the common carrier for each holding device and correspondingly associated container on the common element. It is preferable for the pre-determined distance a to be reached or for it to be present respectively when the holding device or the follower element (such as for example a cam roller) travel or reach respectively the highest point/area of the lifting cam.

It is preferable for the sterilization devices and the holding devices (or the common carrier as well as the common element respectively) to be rotated about the axis of rotation E, which is identical for both devices. In the same way, the devices are rotated or moved respectively at an identical (rotational) speed about this axis of rotation E.

It is particularly preferred for the common carrier and the common element to be arranged on an axle by which the rotation is capable of being produced. It could also, however, be preferred for a respective drive or a respective drive element to be present for the common element or the common carrier.

In the case of a further preferred embodiment the movement device has a mechanical displacement element, an hydraulic or pneumatic drive or an electric motor, in particular a linear motor, so that the movement of the common carrier on which the plurality of sterilization devices are arranged is capable of being produced in the longitudinal direction L by this apparatus element.

In this way, by means of the present apparatus a mutually independent movement between the radiation finger/sterilization device and the containers or the holding devices/clamps thereof respectively or the lifting cam is preferably made possible/capable of being achieved. In this case it is preferable for the radiation finger to be moved only in the longitudinal direction L, whilst no driving/no sterilization takes place, since this movement is required for the adjustment to the container or the pre-form and not for the sterilization process or the sterilization procedure respectively, since the movement of the containers or the holding devices respectively is used or is sufficient respectively on account of the lifting cam.

In the case of a further preferred apparatus a detection device or measuring device respectively is present (for example a laser device) which can detect and process the length of the respective containers to be sterilized. In addition, it is preferable for a calculator unit to be present, which is designed and arranged in such a way as to be able to refer back to the (currently) relative distance r or to process and/or use it respectively. It is particularly preferred for the calculator unit to compare and/or calculate—on the basis of the relative distance r and the length detected by the detection device or measuring device respectively—how far a base of the container will approach the outlet window and initiate an emergency stop of the apparatus if it becomes apparent that the base of the container could collide or come into contact with the outlet window (or if the calculator unit is designed and arranged in the manner specified respectively). Instead of or in addition to an emergency stop, a raising of the carrier could also be initiated with the sterilization devices with respect to the lifting cam.

In the case of a further advantageous embodiment the apparatus has a clean room or forms a clean room respectively, inside which the plastics material containers are conveyed during the sterilization thereof. In this case it is preferable for this clean room to be sealed off from an environment by means of at least one wall. It is preferable for the clean room to be set under an over-pressure or for the clean room to be capable of being set under an over-pressure respectively with respect to the (non-sterile) environment.

It is advantageous for the aforesaid common carrier of the plurality of sterilization devices also to form a wall of this clean room. In this case it is preferable for only the radiation finger or the rod-like body respectively to be capable of extending into the clean room or of being arranged in the latter and for the further units of the sterilization device to be arranged outside the clean room. In the case of a further advantageous embodiment the apparatus has a sealing device in order to seal this clean room off from an environment. This sealing device can be for example a so-called surge chamber which preferably has a circumferential duct which is capable of being filled with a liquid medium and into which a wall element dips and is movable with respect to the latter.

In the case of a further embodiment the sealing of the clean room is carried out by a circumferential suction duct. In this case air is sucked both out of the interior space or clean room respectively and out of the surrounding room.

The arrangement of the lifting cam outside the clean room is also advantageous in the design of the clean room. The follower element including a roller is arranged outside the clean room in this case, and the holding device is sealed off from the environment by means of a sealing element such as an elastomer bellows or metal bellows or similar sealing elements suitable for a clean room.

In the case of a further advantageous embodiment the apparatus also has screening elements in order to prevent radiation, in particular x-ray radiation, from escaping from the plant. These can preferably also be elements/walls of the clean room or the clean room boundary respectively.

In the case of a preferred embodiment the sterilization device also has a cooling device for cooling the outlet window. In this case it is possible for the rod-like body/the radiation finger to have a duct through which a medium, in particular a gaseous medium, can be conveyed in the direction of the outlet window. It is advantageous for this gas flow or the gaseous medium respectively for cooling the outlet window to be removed at least in part and preferably completely from the clean room. It is advantageous for the outlet window to be an outlet window of titanium which in a particularly preferred manner has a thickness which is between 7 and 13 μm. In the case of a further advantageous embodiment the apparatus has a deflecting device which, in particular, conveys the gaseous medium to the aforesaid area of the outlet device. It is preferable if the gas flow/the gaseous medium can be an air flow, such as for example a sterile air flow. It would also be possible, however, for an atmosphere of other gases to be provided in the clean room, such as for example a nitrogen atmosphere.

It is preferable for the air removed from the clean room (or in general the gaseous medium removed) to be tempered and, in particular, cooled before it is supplied to the individual outlet windows. In this case heat exchangers, as known per se from the prior art, can be used for cooling this air.

It is particularly preferred for the cooling device to have a first stressing device, which cools a first area of the outlet window with a liquid medium, and a second stressing device, which cools a second area of the outlet window with a gaseous medium. Cooling with the liquid medium or the gaseous medium respectively is to be understood as meaning that the outlet window needs not necessarily be acted upon itself with this medium, but that for example cooling ducts can also be provided through which the respective cooling medium flows. A direct stressing of the outlet window or an area thereof respectively—in particular with respect to the gaseous medium—is also, however, possible. In principle it would also be possible for a cooling of the various areas to be carried out in each case with a gaseous medium, i.e. for the two areas to be cooled in each case by means of a gaseous medium.

In the case of a further advantageous embodiment a collision prevention device is provided which has a contact body which—in particular in the event of an incorrect positioning of the container and/or a holding device for holding the container occurring—prevents a collision of the rod-like body with the container, in particular the aperture of the container. In this way, in the case of this embodiment, in particular, a collision of the rod-like body with the container itself and/or the holding device thereof should be prevented.

In practice it can happen that the holding or gripping elements which hold the containers do not get hold of the latter properly and the containers lie obliquely for example in the holding elements. In this situation it is possible that the rod-like body collides by the feed movement of the container to the rod-like body with the container. Just this collision can be sufficient to damage the rod-like body in a lasting manner.

A collision of this type can be prevented by the aforesaid contact body. In this way, it is possible for the apparatus to stop the feed movement in the event of an occurrence of a mechanical contact of this type between the container and the contact body. It would also be possible, however, for the holding element to release the container in reaction to a contact of this type, so that the latter can no longer come into contact with the rod-like body.

It is therefore preferable for this contact body to be arranged in such a way that the contact body contacts the container before the rod-like body contacts the container. It is preferable for the contact body to have a tubular body which surrounds the rod-like body at least in sections. On the one hand the rod-like body is protected against knocks in its radial direction by this tubular body, and on the other hand it is possible for this tubular body to touch, in particular, obliquely positioned plastics material containers before the rod-like body touches them.

In the case of a further advantageous embodiment a switching device is provided which has the effect that in the event of contact between the contact body and the plastics material container and/or the holding device for the plastics material container the feed movement of the plastics material container is stopped. It is advantageous for a discharge device to be provided which discharges containers arranged on the holding device in an incorrect manner.

The present invention further relates to a method for the sterilization of containers in which in order to sterilize the containers the containers are conveyed over a rod-like body and in the interior of the containers an inner wall of the containers is acted upon with radiation and in which the containers are moved by a lifting cam with respect to the rod-like body in a longitudinal direction L of the containers in order to introduce the rod-like body into the container through the aperture thereof. A guidance of the containers over the rod-like body is to be understood as being that the rod-like bodies dip or are introduced respectively at least in sections into the containers or the inner space thereof respectively.

In accordance with the method according to the invention the lifting cam and the rod-like body are moved relative to each other in the longitudinal direction L of the containers and a relative distance r between the lifting cam and the rod-like body is altered.

In accordance with a preferred method the relative distance r between the lifting cam and the rod-like body is altered in such a way that a pre-determined distance a between a base area of the containers and the rod-like body is set.

It is preferable for the containers to be conveyed along a pre-set conveying path, while the containers are sterilized. In addition, it is preferable for a movement device to be provided which moves the lifting cam and the rod-like body relative to each other. It is particularly preferred in this case for the movement device to move only the rod-like body or the sterilization device respectively.

In the case of a further preferred method a plurality of sterilization devices are arranged with the rod-like bodies or the radiation fingers thereof respectively on a common carrier which is moved by the movement device with respect to the lifting cam in the longitudinal direction L. It is preferable for a movement of the containers, which are arranged on a common element by way of a plurality of respective holding devices or holding clamps respectively, to be carried out by the design of the lifting cam.

In addition, it is preferable for the sterilization to be carried out in the region in which the lifting cam is raised, so that an activation of the sterilization devices could be activated or deactivated respectively in a manner dependent upon the position thereof and the position of the containers, so that the sterilization device is activated only when the container is present at a specific distance below the rod-like body or the radiation finger respectively or only as soon as the latter is already situated at least in part in the container.

BRIEF DESCRIPTION OF THE DRAWINGS

Further advantages and embodiments are evident from the accompanying drawings. In the drawings

DETAILED DESCRIPTION OF THE INVENTION

Figure 1:
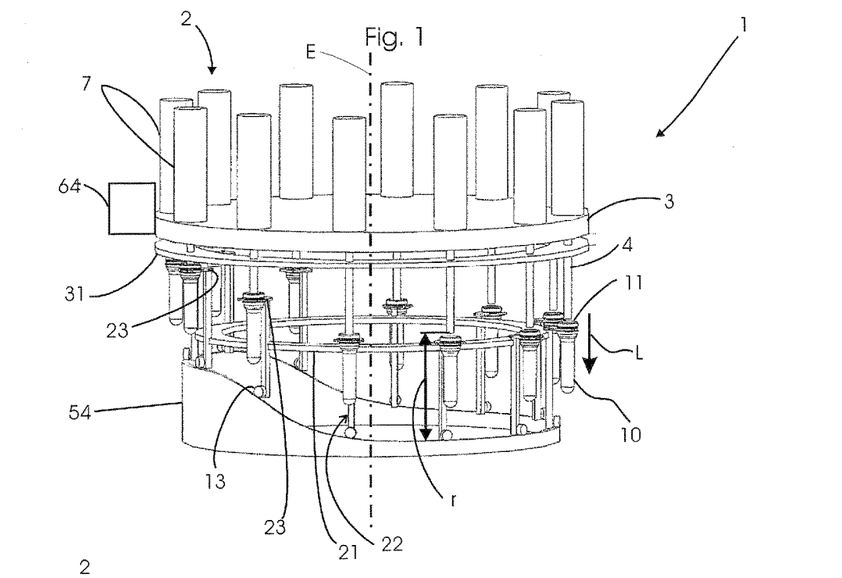
FIG. 1 is a diagrammatic illustration of an apparatus according to the invention for the sterilization of containers.

FIG. 1 is a diagrammatic illustration of an apparatus 1 according to the invention for the sterilization of containers 10. As mentioned above, however, in this case the containers 10 could also (preferably) be plastics material pre-forms 10. The containers 10 extend in this case in a longitudinal direction L and have an aperture 11 through which rod-shaped bodies 4 or radiation fingers 4 respectively can be guided into the containers. A plurality of containers 10 are arranged in this case on a common element 21. The latter is designed in this case in the form of an annual carrier 21, but any design would be possible.

The containers 10 are gripped or held respectively below the carrying rings 19 thereof (See FIG. 3) by clamps 23, the clamps 23 being an element portion of a holding device 22, thus being arranged on a holding device 22, and in turn are fastened, arranged in a movable manner (in particular in the longitudinal direction L thereof) on the common element 21. A follower element 13, such as for example a cam roller, is provided at the lower end of the holding device 22.

This follower element 13 runs on or follows respectively a preferably pre-set, fixed lifting cam 54. This lifting cam 54 is designed and arranged in such a manner that it produces or can produce respectively a vertically reciprocating movement of the follower element 13 and thus of the containers 10. In this case it may be seen from FIG. 1 that this results from a different vertical design of the lifting cam 54. The follower elements need not necessarily, however, run (along) on the lifting cam 54, as shown in FIG. 1, but other possibilities would also be possible for the lifting cam 54, for example a groove in which the follower element 13 is moved/runs. In addition, a spring element (not shown) which pre-stresses the follower element 13 with respect to or on the lifting cam could possibly be provided.

The movement of the containers 10 takes place in a circular manner about an axis of rotation E in FIG. 1. Other possibilities of movement would also, however, be conceivable, such as for example elliptic or, however, by way of a common element 21 designed in a different manner, for example in the manner of a conveying device which provides straight-line or free possibilities of movement. Accordingly, the lifting cam 54 and the further elements (for example the common carrier 3) would also have to be designed differently.

In addition, the apparatus 1 has in this case a common carrier 3 on which are fastened/arranged a plurality of sterilization devices 2 with the corresponding radiation fingers or rod-like bodies 4 respectively. This common carrier 3 is also rotatable in this case about the axis of rotation E, and so the axes about which the common carrier 3 and the common element 21 rotate are substantially congruent or parallel to each other respectively and overlapping, so as to result in a common axis of rotation E. The further elements of the sterilization device 2, which can be inter alia charge carrier generators/electron generators and charge carrier accelerators/electron accelerators, are designated roughly diagrammatically with the reference number 7.

In addition, a centre axis or axis of symmetry K respectively of the radiation finger (see FIG. 3) is in the same distance away from the axis of rotation E as a centre axis or axis of symmetry S respectively of the container 10. The containers 10 and the radiation fingers 4 are substantially rotationally symmetrical in this case. In the same way, these two axes S, K extend parallel to each other, and this likewise results in a parallelism with the longitudinal direction L of the container. As may be seen from FIG. 1, the same number of sterilization devices 2 are present or arranged respectively on the carrier 3 as also the same number of holding devices 22 with corresponding containers 10 on the element 21. It follows from this that a sterilization device 2 is thus present for each container 10. The axes S and K are not only parallel in this case but overlap each other or are congruent respectively, so that as secure as possible a movement/guidance of the container 10 can take place by way of the radiation fingers 4.

In addition, this longitudinal direction L is also in this case the acceleration direction in which the charge carriers/electrons are accelerated and/or the direction of movement in which the charge carriers/electrons preferably move inside the radiation finger 4.

A movement device which in this embodiment can move or displace the entire "plate" or the common carrier 3 respectively in the longitudinal direction L or can produce a relative movement in the longitudinal direction L, in particular between the radiation finger 4 and the lifting cam 54, is designated purely diagrammatically with the reference number 64. In this way, the height of the common carrier 3 or a relative distance r (which in this case is designated by way of example with the double arrow in a diagrammatic manner) between the common carrier 3, the sterilization devices 2 and the radiation fingers 4 respectively can be altered or adjusted by the movement device 64. The distance must always be observed at one and the same point on the lifting cam 54 in this case, since the extension thereof in the longitudinal direction L changes. According to the present embodiment therefore, not only the extension of the lifting cam in the longitudinal direction L is fixed, but likewise the arrangement of the lifting cam 54 itself, it accordingly being preferable for the lifting cam 54 not to be capable of being moved in the longitudinal direction L.

The arrangement of the movement device 64 is selected in a non-restrictive manner in FIG. 1 and in the same way is purely diagrammatic, for example a shaft (not shown) could be present and present about the axis of rotation E, on which both the carrier 3 and/or the common element 21 are fastened and on which in the same way the movement device is arranged or at least supported, so that a displacement/movement in the longitudinal direction L of the carrier 3 takes place on this shaft by way of the movement device.

The movement device 64 could also, however, be supported on a further annular element 31 which is arranged on the apparatus 1 in a fixed manner. In FIG. 1 the radiation fingers 4 extend in a movable manner through this annular element 31.

The left-hand area of the lifting cam 54 in FIG. 1 constitutes in this case the highest point which the containers can reach. In this way, the distance between a container base 9 and the radiation finger, and in particular the outlet window 14 thereof, is smallest in this area. This occurs in particular at the reversal point at which the movement in the longitudinal direction L of the container 10 (and towards the latter) is changed over the radiation finger 4 into a movement of the container 10 down from the radiation finger. In this case care must naturally be taken to ensure that this change in movement need not or cannot take place in direct succession, but that the container 10 can be held at this reversal point over a certain period of time, as may be seen in particular in the left-hand region of FIG. 1 in which the lifting cam 54 has a constant rise over a relatively long portion until this rise subsides again. This reversal point, which constitutes the smallest distance occurring between the outlet window 14 and the container base 9 (or which should constitute it in normal operation respectively), is present at the pre-determined distance a between the container base 9 and the outlet window 14 or the radiation finger 4 respectively.

Figure 2:
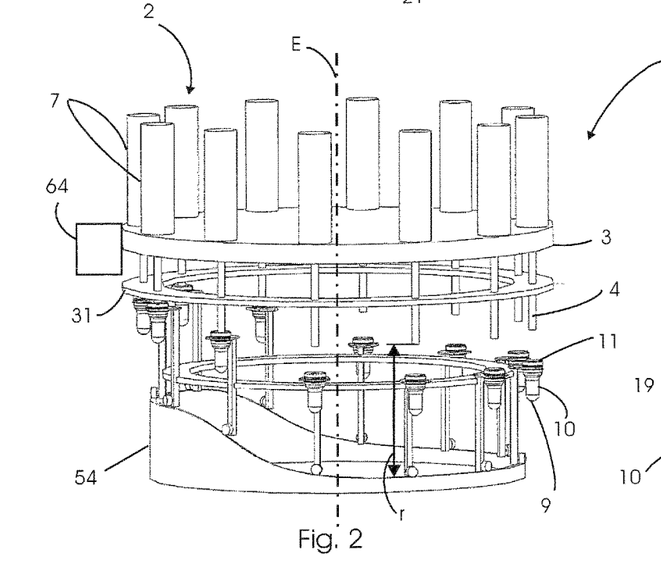
FIG. 2 is a further diagrammatic illustration of an apparatus according to the invention for the sterilization of containers.

In FIG. 2 essentially the same apparatus 1 is shown as in FIG. 1. In this case, however, containers 10 are provided which have a shorter extension in the longitudinal direction L and which are therefore shorter. If they were now to be supplied to the apparatus 1 as shown in FIG. 1, the base area 9 of the containers 10 would collide with the radiation finger 4 introduced in each case, and this could possibly result in an inability to function or destruction of this radiation finger 4 and/or the corresponding radiation device 2. In FIG. 2 the common carrier 3 has therefore been arranged at a greater distance from the lifting cam 54 by the movement device 64. The relative distance r between the lifting cam 54 and the carrier 3 or the radiation finger 4 respectively has thus been enlarged. As a result, it is possible to ensure or it has been ensured respectively that the pre-determined distance a, even in the case of the shorter container 10 (in contrast to FIG. 1), is in turn substantially identical or equal, as a result of which damage to the sterilization device can be prevented, and nevertheless an adequate sterilization of the interior space/the inner wall of the container is capable of being achieved.

The change in the relative distance r can also be derived from the diagrammatic movement device 64 at which—in contrast to FIG. 1—the arrangement of the common carrier 3 has changed in the same way.

Figure 3:
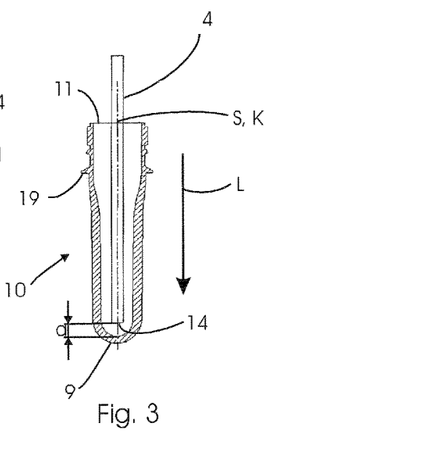
FIG. 3 is a diagrammatic illustration of a radiation finger or a rod-like body respectively over which a container is guided.

FIG. 3 is a cross-section of a container or a pre-form 10 respectively, which is guided over a radiation finger 4. In this case the axes of symmetry S and K can also, in particular, be seen, which are identical/extend in an identical manner and which extend parallel to the longitudinal direction L. At the lower end of the radiation finger the reference number 14 designates in this case the outlet window 14 from which the charge carriers/electrons escape from the radiation finger 4 in order to be able to produce a sterilization of the inner wall of the pre-form 10.

In addition, it is readily evident that the distance a extends between the outlet window 14 and the lowest point or middle point respectively of the container base 9. This middle point is essentially where the axis of symmetry S of the container intersects the inner wall of the base area 9. The carrying ring of the pre-form 10, under or over which the clamp 23 of the holding device 22 grips or holds respectively the pre-form 10, is designated with the reference number 19. In the same way the aperture 11 of the container 10 is visible.

The Applicants reserve the right to claim all the features disclosed in the application documents as being essential to the invention, insofar as they are novel either individually or in combination as compared with the prior art.

All the features disclosed in the application documents are claimed as being essential to the invention, insofar as they are novel either individually or in combination as compared with the prior art.

LIST OF REFERENCES 1 apparatus
2 sterilization device 3 common carrier
4 rod-like body/radiation finger
7 diagrammatic, further elements of the sterilization device
9 container base, pre-form base
10 (plastics material) containers or pre-forms respectively
11 aperture
13 follower element
14 outlet window
19 carrying ring
21 common element/annular carrier
22 holding device
23 clamp
31 annular element
54 lifting cam
64 movement device
a distance between the base area and the radiation finger/outlet window
E axis of rotation
L longitudinal direction
r relative distance between the lifting cam and the radiation finger/outlet window
S axis of symmetry of the container
K axis of symmetry of the rod-like body/radiation finger

The invention claimed is:

1. An apparatus for the sterilization of containers, comprising, in combination, a plurality of sterilization devices arranged on a common carrier rotatable about an axis of rotation (E), wherein the common carrier is movable by a movement device in the longitudinal direction (L) of the containers, each sterilization device having a rod-like body which is capable of being introduced through an aperture of the containers into an interior space of the containers and which acts upon an inner wall of the containers with radiation, and a lifting cam which produces a movement in a longitudinal direction (L) of the containers between the containers and the sterilization device such that the containers are capable of being guided over the rod-like body, wherein the movement device is capable of producing a relative movement in the longitudinal direction (L) of the containers between the rod-like body and the lifting cam and of altering a relative distance (r) between the lifting earn and the rod-like body.

2. The apparatus according to claim 1, wherein the movement device is designed and arranged such that a pre-determined distance (a) between a base area of the containers and the rod-like body is capable of being set.

3. The apparatus according to claim 2, wherein the pre-determined distance (a) is not capable of being altered during operation of the apparatus.

4. The apparatus according to claim 2, wherein the rod-like body has an outlet window for charge carriers produced by the sterilization device, by which outlet window the charge carriers escape from the rod-like body, and the inner wall of the containers is acted upon with the charge carriers, and wherein the pre-determined distance (a) between a base area of the containers and the outlet window of the rod-like body is capable or being set.

5. The apparatus according to claim 1, wherein the sterilization device and/or the rod-like body is movable by the movement device in the longitudinal direction (L) of the containers.

6. The apparatus according to claim 1, wherein the containers are fastened by way of a respective holding device to a common element which is rotatable about an axis of rotation (F) and the respective holding device is movable in the longitudinal direction (L).

7. The apparatus according to claim 6, wherein a follower element which runs on the lifting cam or follows it is arranged on each holding device, as a result of which the relative movement in the longitudinal direction (L) of the containers is capable of being produced.

8. The apparatus according to claim 1, wherein the movement device has a mechanical displacement element, an hydraulic or pneumatic drive or an electric motor.

9. The apparatus according to claim 8, wherein the electric motor comprises a linear electric motor.

10. The apparatus according to claim 1, wherein the rod-like body and lifting cam are arranged on opposite sides of a holding device for holding the containers.

11. The apparatus according to claim 10, wherein the holding device extends from clamps to the lifting cam in the longitudinal direction.

12. The apparatus according to claim 10, wherein the rod-like body has a main extension direction which is parallel to a main extension direction of the holding device.

13. The apparatus according to claim 10, wherein the holding device is rod-shaped.

14. The apparatus according to claim 1, wherein the containers are preforms.

15. The apparatus according to claim 1, wherein the rod-like body is introduced into the containers from above.

16. The apparatus according to claim 1, wherein the containers are held upright.

17. The apparatus according to claim 1, wherein the longitudinal direction (L) is the same as an acceleration direction in which charge carriers/electrons are accelerated from the sterilization device.

18. The apparatus according to claim 1, wherein the sterilization device includes a radiation finger, and the longitudinal direction (L) is same as a direction of movement in which charge carrier/electrons move inside the radiation finger.

19. A method for the sterilization of containers using the apparatus of claim 1, wherein the containers are conveyed over a rod-like body and in the interior of the containers an inner wall of the containers is acted upon with radiation and wherein the containers are moved by a lifting cam with respect to the rod-like body in a longitudinal direction (L) of the containers in order to introduce the rod-like body into the container through the aperture thereof, wherein the lifting cam and the rod-like body are moved relative to each other in a longitudinal direction (L) of the containers and a relative distance (r) between the lifting cam and the rod-like body is altered.

* * * * *

UNITED STATES PATENT AND TRADEMARK OFFICE
CERTIFICATE OF CORRECTION

PATENT NO. : 9,782,503 B2
APPLICATION NO. : 14/632097
DATED : October 10, 2017
INVENTOR(S) : Knott

Page 1 of 1

It is certified that error appears in the above-identified patent and that said Letters Patent is hereby corrected as shown below:

In the Claims

Claim 6, Column 14, Line 8 "rotation (F)" should be --rotation (E)--

Signed and Sealed this
Thirteenth Day of February, 2018

Andrei Iancu
*Director of the United States Patent and Trademark Office*